(12) United States Patent
Chung

(10) Patent No.: US 11,026,983 B2
(45) Date of Patent: Jun. 8, 2021

(54) BIFIDOBACTERIUM BREVE CBT BR3 STRAIN FOR PROMOTION OF GROWTH AND NUTRACEUTICAL COMPOSITION FOR PROMOTION OF GROWTH CONTAINING THE SAME

(71) Applicant: Cell Biotech Co., Ltd., Gimpo-si (KR)

(72) Inventor: Myung Jun Chung, Seoul (KR)

(73) Assignee: Cell Biotech Co., Ltd., Gimp-si (KR)

( * ) Notice: Subject to any disclaimer, the term of this patent is extended or adjusted under 35 U.S.C. 154(b) by 179 days.

(21) Appl. No.: 16/382,669

(22) Filed: Apr. 12, 2019

(65) Prior Publication Data

US 2019/0298784 A1  Oct. 3, 2019

Related U.S. Application Data

(62) Division of application No. 15/310,289, filed as application No. PCT/KR2015/007226 on Jul. 13, 2015, now abandoned.

(30) Foreign Application Priority Data

May 21, 2015  (KR) .......................... 10-2015-0071123

(51) Int. Cl.
| | | |
|---|---|---|
| *A61K 35/745* | (2015.01) | |
| *A23L 33/135* | (2016.01) | |
| *C12N 1/20* | (2006.01) | |
| *C12R 1/01* | (2006.01) | |

(52) U.S. Cl.
CPC .......... *A61K 35/745* (2013.01); *A23L 33/135* (2016.08); *C12N 1/20* (2013.01); *C12R 1/01* (2013.01)

(58) Field of Classification Search
None
See application file for complete search history.

(56) References Cited

U.S. PATENT DOCUMENTS

| | | | |
|---|---|---|---|
| 6,706,287 B2 | 3/2004 | Ranganathan et al. | |
| 6,974,594 B2 | 12/2005 | Ko et al. | |
| 8,715,769 B2* | 5/2014 | Schmitt ................ | A23C 9/1234 426/658 |
| 10,597,740 B2* | 3/2020 | Chung .................. | A23L 33/135 |

FOREIGN PATENT DOCUMENTS

| | | |
|---|---|---|
| EP | 1514553 | 3/2005 |
| KR | 10-0472865 | 3/2005 |
| KR | 10-0530211 | 11/2005 |
| KR | 10-0561286 | 3/2006 |
| KR | 10-0865363 | 10/2008 |
| KR | 10-0887377 | 3/2009 |

OTHER PUBLICATIONS

Kang et al. Korean Journal of Microbiology, 2013, vol. 49, No. 3, pp. 275-281.*
International Search Report, issued in the corresponding International Application No. PCT/KR2015/007226, dated Aug. 26, 2015, 3 pages.
Lee et al., "In Vitro Evaluation of Antimicrobial Activity of Lactic Acid Bacteria against Clostridium difficile", Toxicological Research, vol. 29, No. 2, pp. 99-106, Jun. 29, 2013.
Kim, "Understanding and utilization of microbial agents for improving livestock environment", Rural Development Administration, Korea National Institute Animal Science, Dec. 2, 2009, 22 pages.
Hwang et al., "Immune Disorders and Its Correlation with Gut Microbiome", Immune Network, vol. 12, No. 4, pp. 129-138, Aug. 2012; available at https://synapse.koreamed.org/Synapse/Data/PDFData/0078IN/in-12-129.pdf.

* cited by examiner

*Primary Examiner* — Vera Afremova
(74) *Attorney, Agent, or Firm* — Hamre, Schumann, Mueller & Larson, P.C.

(57) ABSTRACT

The present invention relates to a novel *Bifidobacterium* strain having an excellent growth promoting effect, and a nutraceutical composition for promotion of growth, which contains the strain. The strain of the present invention has a beneficial effect of promoting growth by promoting the digestion of human milk oligosaccharides to enhance immunity together with physical strength.

5 Claims, 7 Drawing Sheets

Specification includes a Sequence Listing.

FIG. 1a

AGAGTTTGATCCTGGCTCAGGATGAACGCAGGCGGCGTGCTTAACACATGCAAGT
CGAACGGGATCCATCGGGCTTTGCTTGGTGGTGAGAGTGGCGAACGGGTGAGTAA
TGCGTGACCGACCTGCCCCATGCACCGGAATAGCTCCTGGAAACGGGTGGTAATG
CCGGATGCTCCATCACACCGCATGGTGTGTTGGGAAAGCCTTTGCGGCATGGGAT
GGGGTCGCGTCCTATCAGCTTGATGGCGGGGTAACGGCCCACCATGGCTTCGACG
GGTAGCCGGCCTGAGAGGGCGACCGGCCACATTGGGACTGAGATACGGCCCAGA
CTCCTACGGGAGGCAGCAGTGGGGAATATTGCACAATGGGCGCAAGCCTGATGCA
GCGACGCCGCGTGAGGGATGGAGGCCTTCGGGTTGTAAACCTCTTTTGTTAGGGA
GCAAGGCACTTTGTGTTGAGTGTACCTTTCGAATAAGCACCGGCTAACTACGTGCC
AGCAGCCGCGGTAATACGTAGGGTGCAAGCGTTATCCGGAATTATTGGGCGTAAA
GGGCTCGTAGGCGGTTCGTCGCGTCCGGTGTGAAAGTCCATCGCTTAACGGTGGA
TCCGCGCCGGGTACGGGCGGGCTTGAGTGCGGTAGGGGAGACTGGAATTCCCGG
TGTAACGGTGGAATGTGTAGATATCGGGAAGAACACCAATGGCGAAAGGCAGGTC
TCTGGGCCGTTACTGACGCTGAGGAGCGAAAGCGTGGGGAGCGAACAGGATTAG
ATACCCTGGTAGTCCACGCCGTAAACGGTGGATGCTGGATGTGGGGCCCGTTCCA
CGGGTTCCGTGTCGGAGCTAACGCGTTAAGCATCCCGCCTGGGGAGTACGGCCGC
AAGGCTAAAACTCAAAGAAATTGACGGGGGCCCGCACAAGCGGCGGAGCATGCG
GATTAATTCGATGCAACGCGAAGAACCTTACCTGGGCTTGACATGTTCCCGACGAC
CCCAGAGATGGGGTTTCCCTTCGGGGCGGGTTCACAGGTGGTGCATGGTCGTCGT
CAGCTCGTGTCGTGAGATGTTGGGTTAAGTCCCGCAACGAGCGCAACCCTCGCCC
CGTGTTGCCAGCGGATTATGCCGGGAACTCACGGGGGACCGCCGGGGTTAACTCG
GAGGAAGGTGGGGATGACGTCAGATCATCATGCCCCTTACGTCCAGGGCTTCACG
CATGCTACAATGGCCGGTACAACGGGATGCGACAGTGCGAGCTGGAGCGGATCCC
TGAAAACCGGTCTCAGTTCGGATCGCAGTCTGCAACTCGACTGCGTGAAGGCGG
AGTCGCTAGTAATCGCGAATCAGCAACGTCGCGGTGAATGCGTTCCCGGGCCTTGT
ACACACCGCCCGTCAAGTCATGAAAGTGGGCAGCACCCGAAGCCGGTGGCCTAA
CCCCTTGCGGGAGGGAGCCGTCTAAGGTGAGGCTCGTGATTGGGACTAAGTCGTA
ACAAGGTAGCCGTACCGGAAGGTGCGGCTGGATCACCTCCTT

BIFIDOBACTERIUM BREVE CBT BR3 STRAIN FOR PROMOTION OF GROWTH AND NUTRACEUTICAL COMPOSITION FOR PROMOTION OF GROWTH CONTAINING THE SAME

CROSS-REFERENCE TO RELATED APPLICATIONS

This application is a Division of application Ser. No. 15/310289, filed Nov. 10, 2016, which is a National Stage application of PCT/KR2015/007226, filed Jul. 13, 2015, which is based upon and claims the benefit of priority from Korean Patent Application No. 10-2015-0071123, filed on May 21, 2015, the contents of which are incorporated herein by reference.

TECHNICAL FIELD

The present invention relates generally to a *Bifidobacterium breve* CBT BR3 strain for promotion of growth and a nutraceutical composition for promotion of growth containing the same, and more particularly to a *Bifidobacterium breve* CBT BR3 strain capable of promoting the growth of neonates, infants and growing children by promoting the digestion of human milk and synthesizing vitamins, and to a nutraceutical composition for promotion of growth, which contains the *Bifidobacterium breve* CBT BR3 strain.

BACKGROUND ART

Human growth occurs in a period up to adolescence, in which most growth plates are still open. Growth can be medically defined as a change in size accompanying maturation, and particularly, the term "growth of children" is intended to encompass not only an increase in height, but also increases in the size and function of each organ of the body.

It is generally recognized that human growth is most influenced by genetic factors. However, in fact, genetic factors have only about 23% of an influence on human growth, and the remaining 77% is determined by postnatal factors. In recent years, due to continued economic growth, westernized eating habits, improved nutritive conditions, etc., the growth and development of children and teenagers has greatly increased. In addition, with the emphasis of a social atmosphere where external appearances and heights are considered important, growth has been of increasing interest.

Methods for promoting growth, known to date, include methods of administering growth hormone agents. However, the use of growth hormones is very costly and may cause adverse effects, including various symptoms such as pruritus of injection sites, seizures, lipoatrophy, hypertension, glucose intolerance, pancreatitis, systemic allergic responses, growth hormone antibody-positive responses, cancer development, and gynaecomastia in males. Accordingly, there is an urgent need for the development of safe and effective food materials that can essentially assist in growth.

Korean Patent No. 0887377 (entitled "Health supplement food for babies and teenagers"), Korean Patent No. 10530211 (entitled "Functional health food composition for improving learning ability and preparation method thereof"), Korean Patent No. 0561286 (entitled "Health functional composition for promotion of growth and development containing dried yeast, natural extract powder and mixed powder of nutritive components"), etc., suggest foods for promotion of growth. However, these foods have insufficient effects on growth promotion.

DISCLOSURE

Technical Problem

The present inventors have made extensive efforts to discover probiotics having excellent growth promoting effects, and, as a result, have experimentally found the applicability of a *Bifidobacterium breve* CBT BR3 strain as a growth-promoting product, thereby completing the present invention. An object of the present invention is to provide a *Bifidobacterium breve* CBT BR3 strain suitable for use for promotion of the growth of neonates, infants, young children, and growing children.

Another object of the present invention is to provide a nutraceutical composition that can promote the growth of infants, children and teenagers by promoting the digestion of human milk oligosaccharides, promoting vitamin synthesis and inhibiting the proliferation of harmful bacteria.

Technical Solution

In order to accomplish the above objects, one aspect of the present invention is directed to the provision of a *Bifidobacterium breve* CBT BR3 *Bifidobacterium* for promotion of growth, internationally deposited with the Korean Collection for Type Culture (KCTC) of the Korea Research Institute of Bioscience and Biotechnology under accession number KCTC 12201BP.

Another aspect of the present invention is directed to the provision of a nutraceutical composition capable of promoting the growth of infants, children and teenagers, which contains the *Bifidobacterium breve* CBT BR3 strain of the present invention.

Advantageous Effects

The *Bifidobacterium breve* CBT BR3 strain of the present invention exhibits an excellent growth promoting effect by digesting and supplying human milk oligosaccharides, which are difficult to industrially produce in large amounts and are not digested by human enzymes, and also promoting vitamin biosynthesis, inhibiting the proliferation of harmful intestinal bacteria, and regulating the immune system.

The nutraceutical composition for promotion of growth according to the present invention may promote the growth and development of neonates, infants, children and teenagers by activating metabolisms in balance and regulating the immune system, and may also promote brain development. In addition, the nutraceutical composition for promotion of growth according to the present invention may alleviate growth retardation, development retardation, deterioration of physical strength, and low body weight.

DESCRIPTION OF DRAWINGS

FIG. 1*a* shows the 16S rRNA gene sequence of a *Bifidobacterium breve* CBT BR3 strain (KCTC 12201BP) according to the present invention (SEQ ID NO: 1);

BEST MODE

Figure 1B:
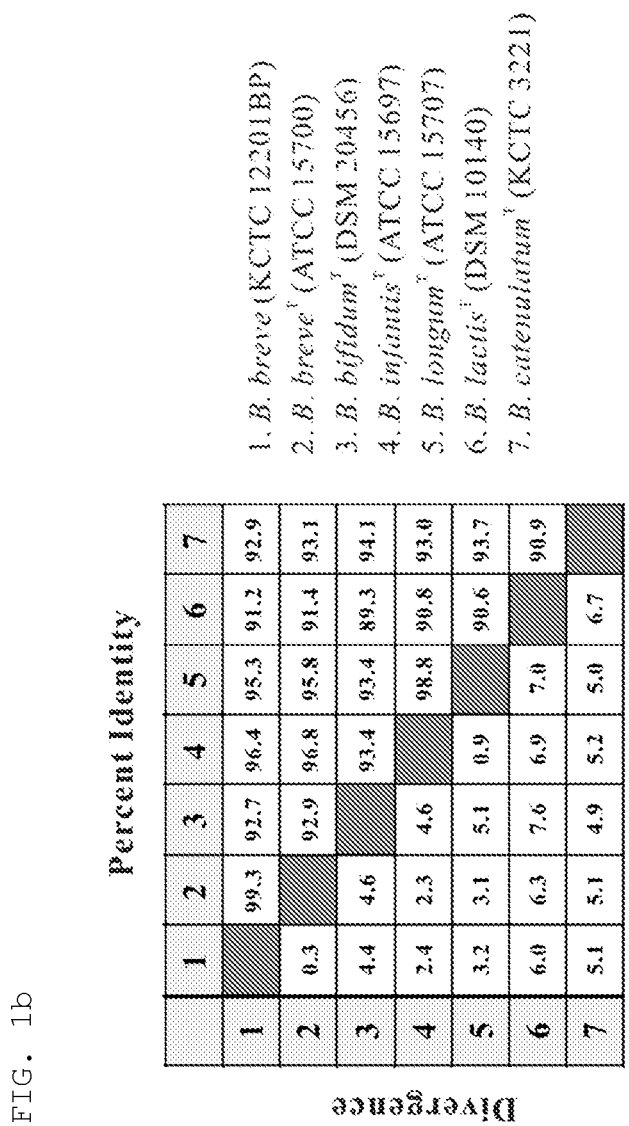
FIGS. 1*b* and 1*c* show the comparisons of the 16S rRNA gene sequence homologies and phylogenetic relationships between the *Bifidobacterium breve* CBT BR3 strain of the present invention and related species.

Hereinafter, the present invention will be described in greater detail.

One aspect of the present invention is directed to a *Bifidobacterium breve* CBT BR3 *Bifidobacterium*, which has an excellent growth promoting effect and was internationally deposited with the Korean Collection for Type Culture (KCTC) of the Korea Research Institute of Bioscience and Biotechnology under accession number KCTC 12201BP.

The *Bifidobacterium breve* CBT BR3 strain according to the present invention can promote growth by digesting human milk oligosaccharides (HMOs), which are not digested by human enzymes and are difficult to industrially produce in large amounts due to their very complex structure, and supplying human milk oligosaccharides to infants or young children who take this strain.

It is known that human milk contains 200 or more kinds of oligosaccharides having useful functions. It is known that human milk oligosaccharides promote the proliferation and propagation of beneficial intestinal microbial flora, inhibit the proliferation of harmful bacteria, function as regulator of cell responses, regulate the immune system, and contribute to the brain development of neonates and infants by supplying brain activity energy as a component essential for the brain growth and development of neonates and infants.

The human milk oligosaccharides have resistance to enzymatic digestion in the upper gastrointestinal tract and in the small intestines, and thus reach the colon without being damaged and function as a substrate for fermentation in the colon. It is thought that human milk contains several factors that promote the proliferation of beneficial intestinal microbial flora that inhibit the proliferation of pathogenic microorganisms. A process of enabling human milk oligosaccharides to increase the number of beneficial bacteria and reduce the number of potentially pathogenic bacteria occurs through competition for cell surface receptors, competition for essential nutrients, production of antibacterial agents, and production of inhibitory compounds such as single-chain fatty acids (SCFAs), which can lower the pH of excrement and inhibit potentially pathogenic bacteria. Human milk oligosaccharides are fermented to produce SCFAs such as acetic acid, propionic acid and butyric acid. It is thought that such SCFAs contribute to calories, function as a major energy source for the intestinal epithelium, stimulate the absorption of sodium and water in the colon, and enhance digestion and absorption in the small intestines. In addition, SCFAs contribute to general gastrointestinal health by regulating gastrointestinal development and immune functions.

Human milk oligosaccharides (HMOs) are composed of various oligosaccharides, mainly five monosaccharides: D-glucose (Glc), D-galactose (Gal), N-acetylglucosamine (GlcNAc), L-fucose (Fuc), and sialic acid (Sia; N-acetylneuraminic acid [Neu5Ac]). The genome of the *Bifidobacterium breve* CBT BR3 strain according to the present invention includes various kinds of genes encoding enzymes that digest human milk oligosaccharides (HMOs). The genome of the *Bifidobacterium breve* CBT BR3 strain according to the present invention includes genes that encode α-mannosidase, β-mannosidase, endo-β-N-acetylglucosaminidase, sialidase, and α-fucosidase.

The *Bifidobacterium breve* CBT BR3 strain according to the present invention includes genes that encode deacetylase, glucoside hydrolase, family 1, β-glucosidase, β-1,3-exoglucanase, thermostable β-glucosidase B, D-allulose-6-phosphate 3-epimerase, sialidase A, UDP-N-acetylglucosamine diphosphorylase, 1,6-α-glucosidase, nucleoside-diphosphate-sugar epimerase, and amylo-α-1,6-glucosidase.

In addition, the genome of the *Bifidobacterium breve* CBT BR3 strain according to the present invention has genes that synthesize vitamins, particularly vitamins of group B. In the genome of the *Bifidobacterium breve* CBT BR3 strain according to the present invention, genes capable of synthesizing two kinds of vitamins exist. Folate (B9) can be synthesized from chorismate, and nicotinic acid (B3) can be synthesized from L-aspartate.

Figure 7:
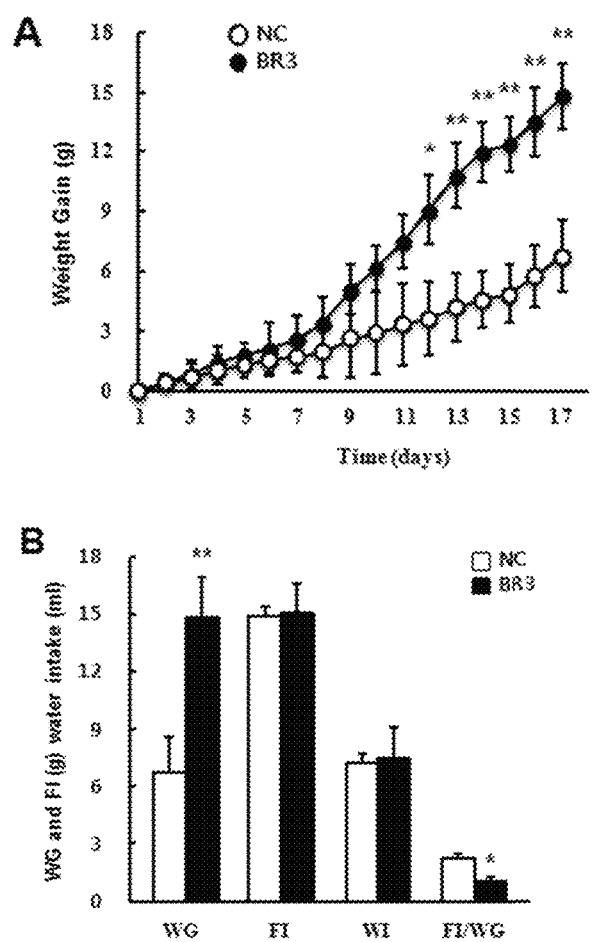
FIG. 7 is a graph showing the growth promoting effect of the *Bifidobacterium breve* CBT BR3 strain of the present invention on mouse growth.

As shown in FIG. 7, the *Bifidobacterium breve* CBT BR3 strain according to the present invention has a gene for biosynthesis of bacteriocin.

According to another aspect of the present invention, the *Bifidobacterium breve* CBT BR3 strain of the present invention may be used as probiotic Bifidobacteria or may be used in various milk products and other fermentation products.

Still another aspect of the present invention is directed to a nutraceutical composition for promotion of growth, which contains the *Bifidobacterium breve* CBT BR3 strain of the present invention. Currently, human milk oligosaccharides (HMOs) cannot be produced in large amounts or are not commercially available, and thus are not contained in most formula milk or formula food products. Although human milk oligosaccharides (HMOs) are essential nutrient sources for infants, these oligosaccharides are not digested by human enzymes, and are excreted as feces if these are not digested. The nutraceutical composition for promotion of growth according to the present invention can promote the brain development and growth of neonates and infants by digesting and supplying human milk oligosaccharides. The food composition is a food, a nutraceutical, a supplement, a probiotic or a symbiotic. The term "probiotic" used herein refers to live microorganisms that are beneficial for the health of the host organism when they supplied in suitable amounts. The term "symbiotic" used herein refers to foods containing a mixture of prebiotic and probiotic.

In some embodiments, the composition of the present invention may further contain, in addition to the *Bifidobacterium breve* CBT BR3 strain, one or more lactic acid bacteria or Bifidobacteria strains selected from the group consisting of *Lactobacillus salivarius, Lactobacillus brevis, Lactobacillus helveticus, Lactobacillus fermentum, Lactobacillus paracasei, Lactobacillus casei, Lactobacillus del-*

*brueckii, Lactobacillus reuteri, Lactobacillus buchneri, Lactobacillus gasseri, Lactobacillus johonsonii, Lactobacillus kefir, Lactococcus lactis, Bifidobacterium bifidum, Bifidobacterium pseudolongum, Bifidobacterium themophilum,* and *Bifidobacterium adolescentis*.

The *Bifidobacterium breve* CBT BR3 strain according to the present invention can be proliferated by culture in a medium that is generally used for culture of Bifidobacteria, and can be recovered after culture. The culture product obtained after culture may be used intact, and, if required, may be subjected to crude purification using centrifugation and/or solid-liquid separation using filtration or a sterilization operation. Preferably, only the Bifidobacteria cells are recovered by centrifugation. In addition, the Bifidobacteria that are used in the present invention may be wet cells or dry cells. For example, the Bifidobacteria may be formulated as a probiotic by lyophilization and used in that state.

The composition of the present invention may further contain, in addition to the *Bifidobacterium breve* CBT BR3 strain, a conventional carrier or excipient. In addition, the composition of the present invention may be formulated with various additives such as binders, disintegrants, coating agents, lubricants and the like.

The composition of the present invention may be formulated in the form of powders, granules, tablets or liquids by mixing the *Bifidobacterium breve* CBT BR3 strain with a suitable carrier, excipient, other active ingredients, etc. In addition, the strain of the present invention may be enteric coated using a known method so that the active ingredient Bifidobacteria will reach the colon after passage through the gastrointestinal tract and will be rapidly released in the intestines.

Excipients that may be used in the present invention include saccharides such as sucrose, lactose, mannitol or glucose, and starches such as corn starch, potato starch or partially pre-gelatinized starch. Binders that may be used in the present invention include polysaccharides such as dextrin, sodium alginate, carrageenan gum, guar gum, acacia gum, agar and the like; naturally occurring macromolecular substances such as tragacanth gum, gelatin, gluten and the like; cellulose derivatives such as hydroxypropyl cellulose, methyl cellulose, hydroxypropylmethyl cellulose, ethyl cellulose, hydroxypropylethyl cellulose, carboxymethyl cellulose and the like; and polymers such as polyvinylpyrrolidone, polyvinyl alcohol, polyvinyl acetate, polyethylene glycol, polyacrylic acid, polymethacrylic acid and vinyl acetate resins.

Disintegrants that may be used in the present invention include cellulose derivatives such as carboxymethylcellulose, carboxymethylcellulose calcium, low-substituted hydroxypropyl cellulose, etc.; and starches such as sodium carboxymethyl starch, hydroxypropyl starch, corn starch, potato starch, rice starch and partially pre-gelatinized starch.

Examples of lubricants that may be used in the present invention include talc, stearic acid, calcium stearate, magnesium stearate, colloidal silica, hydrous silicon dioxide, various kinds of waxes and oils, etc.

Coating agents that may be used in the present invention include water-insoluble polymers such as dimethylaminoethylmethacryklate-methacrylic acid copolymers, polyvinylacetaldiethylaminoacetate, ethylacrylate-methacrylic acid copolymers, ethylacrylate-methylmethacrylate-chlorotrimethyl ammonium ethylmethacrylate copolymers, ethylcellulose, etc.; enteric polymers such as methacrylic acid-ethylacrylate copolymers, hydroxypropylmethylcellulose phthalate, hydroxypropylmethylcellulose acetate succinate, etc.; and water-soluble polymers such as methylcellulose, hydroxypropyl methylcellulose, polyvinylpyrrolidone, polyethylene glycol, etc., but are not necessarily limited thereto.

The content of the active ingredient *Bifidobacterium breve* CBT BR3 strain in the composition for promotion of growth according to the present invention can be suitably determined in view of the subject's weight, age or sex. For example, the composition of the present invention contains, as an active ingredient, the *Bifidobacterium breve* CBT BR3 strain at a nutritionally effective concentration relative to the total weight of the composition. Preferably, the composition contains the *Bifidobacterium breve* CBT BR3 strain in an amount of $10^8$ to $10^{12}$ cfu/g or contains a culture product having the same number of live bacteria. Generally, for adults, $1\times10^6$ or more live bacteria, preferably $1\times10^8$ to $1\times10^{12}$ live bacteria, may be administered once or several times as needed.

In still another aspect, the nutraceutical composition for promotion of growth according to the present invention may further contain one or more other prebiotics selected from the group consisting of *Bifidobacterium longum* bv. *infantis* BT1 (KCTC 11859BP), *Bifidobacterium bifidum* BF3 (KCTC 12199BP), and *Bifidobacterium longum* BG7 (KCTC 12200BP). This composition may contain each *Bifidobacterium* strain at the same percentage.

Hereinafter, the present invention will be described with reference to examples. It is to be understood, however, that these examples are only for illustrative purposes and are not intended to limit the scope of the present invention.

EXAMPLES

Example 1

Isolation and Identification of *Bifidobacterium breve* CBT BR3 Strain 1-1: Selection of Strain 1 g of human feces was serially diluted in sterile anaerobic water, and 1 ml of each of the dilutions was poured on Man-Rogosa-Sharpe (MRS. BD. USA) solid medium and cultured for 3 days under anaerobic conditions. The produced colonies were transferred to a lactic acid bacteria selective medium (BL solid medium) obtained by adding BCP (Bromocresol purple, 0.17 g/L) to MRS, and then cultured for 3 days under the same conditions. The BCP indicator changes from purple to yellow when lactic acid bacteria form lactic acid to lower the surrounding pH. Colonies, the color around which changed to yellow, were selected, and then biochemical and molecular biological identification of the selected colonies was performed. Thereafter, one strain having the best functionality and stability was selected.

1-2: Identification of Selected Strain 1) Biochemical Identification Using API Kit In order to examine the sugar utilization of the selected strain, API 50 CHL Carbohydrate Test Kit (bioMerieux Co., France) was used. The strain was cultured in 10 ml of MRS (Man-Rogosa-Sharpe) liquid medium at 37° C. for 17 hours, and then 1 ml of the culture was recovered and washed twice with CHL solution. Next, the cells were collected by centrifugation (MICRO-17, Hanil, Korea) and resuspended in 9 ml of CHL solution. 150 μl of the strain suspension was placed in each well of the API 50 CHL kit, and then autoclaved paraffin oil was dispensed onto the strain suspension in each well. After culture at 37° C. for 3 days, the utilization of each sugar was analyzed. Whether the strain would utilize each of 49 carbon sources was determined by observing whether the color was changed by microbial proliferation. The results of identification were analyzed using the program API web for identification, and the results of the analysis are shown in Tables 1 and 2 below:

TABLE 1

| No. | Carbohydrates | Utilized |
|---|---|---|
| 0 | Control | − |
| 1 | Glycerol | − |
| 2 | Erythritol | − |
| 3 | D-Arabinose | − |
| 4 | L-Arabinose | − |
| 5 | Ribose | + |
| 6 | D-Xylose | − |
| 7 | L-Xylose | − |
| 8 | Adonitol | − |
| 9 | β-Methyl-xyloside | − |
| 10 | Galactose | w |
| 11 | D-Glucose | + |
| 12 | D-Fructose | w |
| 13 | D-Mannose | w |
| 14 | L-Sorbose | − |
| 15 | Rhamnose | − |
| 16 | Dulcitol | − |
| 17 | Inositol | − |
| 18 | Mannitol | − |
| 19 | Sorbitol | − |
| 20 | α-Methyl-D-mannoside | − |
| 21 | α-Methyl-D-glucoside | w |
| 22 | N-Acetyl glucosamine | − |
| 23 | Amygdaline | − |
| 24 | Arbutine | w |
| 25 | Esculine | + |
| 26 | Salicine | w |
| 27 | Cellobiose | − |
| 28 | Maltose | + |
| 29 | Lactose | + |
| 30 | Melibiose | + |
| 31 | Saccharose | + |
| 32 | Trehalose | + |
| 33 | Inuline | − |
| 34 | Melezitose | − |
| 35 | D-Raffinose | + |
| 36 | Amidon | − |
| 37 | Glycogene | − |
| 38 | Xylitol | − |
| 39 | β-Gentiobiose | − |
| 40 | D-Turanose | w |
| 41 | D-Lyxose | − |
| 42 | D-Tagatose | − |
| 43 | D-Fucose | − |
| 44 | L-Fucose | w |
| 45 | D-Arabitol | − |
| 46 | L-Arabitol | − |
| 47 | Gluconate | − |
| 48 | 2-Ceto-gluconate | − |
| 49 | 5-Ceto-gluconate | w | w; weak change

TABLE 2

| | B. breve CBT BR3 (KCTC12201BP) | B. breve* (ATCC 15700) | B. longum* (ATCC 15707) | B. infantis* (ATCC 27920) |
|---|---|---|---|---|
| D-Ribose | + | + | + | − |
| L-Arabinose | − | − | + | − |
| Lactose | + | + | + | + |
| Cellobiose | − | d | − | − |
| Melezitose | − | d | + | − |
| Raffinose | + | + | + | + |
| Sorbitol | − | d | − | − |
| Gluconate | − | − | − | − | d; fermented slowly in the case of positive.

2) Identification by 16s rRNA Gene Sequencing

Genomic DNA was extracted from the isolated strain and subjected to 16s rRNA gene sequencing. Genomic DNA was extracted from 1 ml of the pure culture of the strain (isolated from feces) by use of an Accuprep genomic extraction kit (Bioneer, Korea). Using the extracted DNA as a template, the 16s rRNA gene region was amplified by PCR (MyCycler, BIO-RAD, USA) using primer F (5'-AAGGAGGT-GATCCAGCC-3')[3] and primer R (5'-AAGGAGGT-GATCCAGCC-3')[3].

Figure 1C:
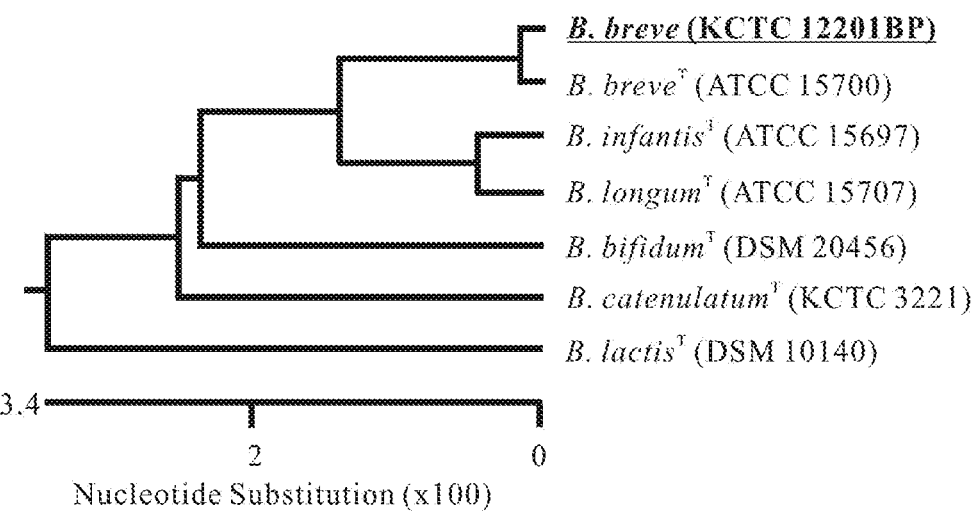

The PCR product was ligated to a pGEM-Teasy vector (Promega, USA) and transformed into an *E. coli* DH5α strain, after which it was plated on an LB/x-gal/amp plate and cultured overnight at 37° C. A recombinant plasmid containing the insert was isolated from the transformant by screening, followed by DNA sequencing. In the DNA sequencing, the homology of the isolated strain to *Bifidobacterium breve*$^T$ (ATCC 15700) was analyzed using the Cluster V method of DNA star program. As shown in FIG. 1, the 16s rRNA gene sequence of the isolated strain showed a homology of 99.3% to *Bifidobacterium breve*$^T$ (ATCC 15700).

3) DNA Fingerprint Analysis by RAPD (Random Amplified Polymorphic DNA)

Figure 2:
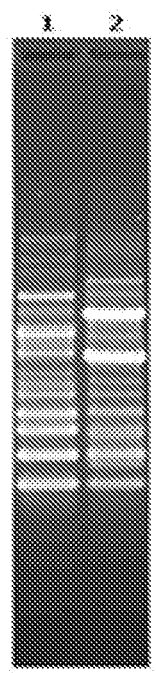
FIG. 2 shows the results of RAPD (Random Amplified Polymorphic DNA) analysis of the genomic DNA of the *Bifidobacterium breve* CBT BR3 strain according to the present invention.

For RAPD analysis, genomic DNA was extracted from the strain isolated from feces. Using the isolated DNA as a template, PCR-RAPD (MyCycler, BIO-RAD, USA) was performed using a $(GTG)_5$ (5'-GTGGTGGTGGTGGTG-3') primer. The resulting PCR product was stained with EtBr (ethidium bromide), and then observed with G:BOX (SYNGENE, UK). As can be seen in FIG. 2, the result of RAPD indicated that the isolated strain showed a band pattern different from that of *Bifidobacterium breve*$^T$ (ATCC 15700). Accordingly, from the above result, it was found that the strain isolated from feces is a strain different from *Bifidobacterium breve*$^T$ (ATCC 15700). In FIG. 2, lane 1 indicates the result for *Bifidobacterium breve*$^T$ (ATCC 15700), and lane 2 indicates the result for the *Bifidobacterium breve* CBT BR3 strain (KCTC 12201BP).

4) DNA Fingerprint Analysis by PFGE (Pulsed Field Gel Electrophoresis)

The O.D. of each of *Bifidobacterium breve* CBT BR3 and *Bifidobacterium breve*$^T$ (ATCC 15700), purely cultured in MRS broth, was measured, and then each strain was adjusted to a final O.D. of $O.D._{600}=4$ using 2% low melting agarose, thereby constructing plugs. The constructed plug was placed in 1 ml of lysozyme buffer (2 mg/ml Lysozyme (Siyma), 0.05% N-lauorylsarcosine (Siyma)), and 10 μl of 4 mg/ml lysostaphin (Sigma) was added thereto, followed by incubation overnight at 37° C. The plug was carefully taken out and was added to 4 ml of NDS buffer (1 ml 1M Tris-HCl (pH=8.0), 10 ml 100% SDS, 89 ml 0.5M EDTA (pH=8.5)), followed by incubation overnight at 50° C. Next, the plug was washed six times with 10 ml of 50 mM EDTA (pH 8.5) with mild shaking, and then was carefully transferred to 400 μl of an enzyme buffer to be treated, followed by incubation at room temperature for 30 minutes. The plug was transferred to 400 μl of fresh enzyme buffer and a restriction enzyme (20 U) was added thereto, followed by incubation overnight at 37° C. As the restriction enzyme, NotI was used. Electrophoresis was performed using a CHEF system (BIO-RAD, USA) in 0.5× TBE at 5.3 cm/V and a pulse time of 1 s to 15 s for 20 hours.

Figure 3:
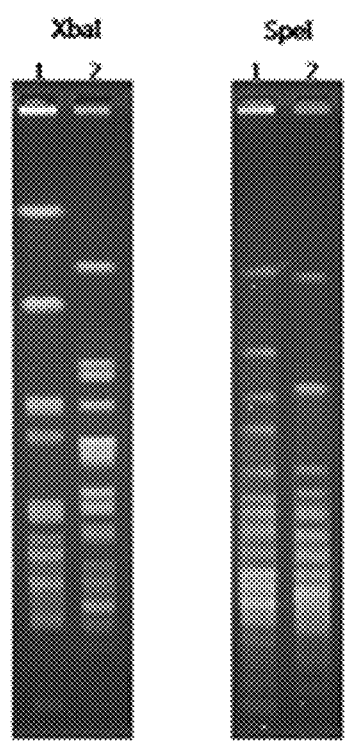
FIG. 3 shows the results of PFGE (Pulsed Field Gel Electrophoresis) analysis of the genomic DNA of the *Bifidobacterium breve* CBT BR3 strain (KCTC 12201BP) according to the present invention.

After completion of electrophoresis, each plug was stained with EtBr solution, and the band pattern thereof was observed with G:BOX (SYNGENE, UK). The results of the PFGE performed using NotI indicated that the *Bifidobacterium breve* CBT BR3 strain isolated from feces was a novel strain showing a band pattern different from that of *Bifidobacterium breve*$^T$ (ATCC 15700). In FIG. 3, lane 1 indicates the result for *Bifidobacterium breve*$^T$ (ATCC 15700), and lane 2 indicates the result for the *Bifidobacterium breve* CBT BR3 strain (KCTC 12201BP).

5) Other Mycological Characteristics

The characteristics of the *Bifidobacterium breve* CBT BR3 strain according to the present invention are as follows:

TABLE 3

1) Morphology of bacteria

The characteristics of the bacteria cultured in MRS agar plate medium at 37° C. for 2 days under oxygen-free conditions.
① type of cells: bacillus
② mobility: none
③ spore forming ability: none
④ gram staining: positive 2) Morphology of colony The morphology of the colony cultured in MRS agar plate medium at 37° C. for 2 days under oxygen-free conditions.
① shape: circular
② raised: convex TABLE 3-continued ③ surface: smooth 3) Physiological properties ① growth temperature: viable growth temperature: 15 to 40° C.
optimum growth temperature: 37° C.
② growth pH: viable growth pH: 5.0-7.5
optimum pH: 6.0-6.5
③ Influence of oxygen: anaerobic

| | |
|---|---|
| 4) Catalase | − |
| 5) Formation of gas | − |
| 6) Growth at 15° C. | − |
| 7) Growth at 45° C. | + |
| 8) Production of indole | − |
| 9) Production of lactic acid | + |

Based on the above-described results, the isolated strain was named "*Bifidobacterium breve* CBT BR3" strain, deposited with the Korean Collection for Type Culture (KCTC), which is an international depository authority, on May 7, 2012, and assigned accession number KCTC 12201BP.

1-3: Functionality and Stability

1) Antibiotic Resistance Test

In order to verify the safety of the isolated *Bifidobacterium breve* CBT BR3 strain (KCTC 12201BP), the antibiotic resistance of the isolated strain was analyzed.

The antibiotic resistance test was performed using the micro-dilution method recommended by the European Food Safety Authority (EFSA), and 10 kinds of antibiotics, including ampicillin vancomycin (VAN), gentamicin (GEN), kanamycin (KAN), streptomycin (STM), erythromycin (ERM), quinupristin/dalfopristin (Q/D), clindamycin (CLM), tetracycline (TET) and chloramphenicol (CP), were used in the test.

For the antibiotics excluding clindamycin, each antibiotic was added to a mixture of 10% ISO-sensitest broth and 90% MRS broth at concentrations of 256, 128, 64, 32, 16, 8, 4, 2, 1, 0.5 μg/ml. Clindamycin was added at concentrations of 16, 8, 4, 2, 1, 0.5, 0.25, 0.125, 0.0625 and 0.03125 μg/ml because the EFSA break point value of the lactobacillus group is 0.25 μg/ml or less. In addition, the test for quinupristin/dalfopristin (Q/D) was performed using an E-test strip (BioMeriux).

Microplates were incubated at 37° C. for 48 hours under anaerobic conditions, and then MIC was measured as the minimum antibiotic concentration at which no visible growth was observed.

Whether *Bifidobacterium breve* CBT BR3 would have resistance to each antibiotic was analyzed, and the results of the analysis are shown in Table 4 below:

TABLE 4

| | Antibiotic (μg/ml) | | | | | | | | | |
|---|---|---|---|---|---|---|---|---|---|---|
| Strain | AMP | VAN | GEN | KAN | STM | ERM | CLM | QU + DA | TET | CP |
| *Bifidobacterium breve* CBT BR3 | <0.5 | <0.5 | <8 | <64 | <32 | <0.5 | <0.06 | <0.38 | <4 | <2 |
| EFSA break point | 2 | 2 | 64 | nr | 128 | 0.5 | 0.25 | 1 | 8 | 4 |

It was shown that the resistances of the isolated *Bifidobacterium breve* CBT BR3 strain to all the antibiotics used in the test were lower than the EFSA antibiotic resistance standards, indicating that the isolated strain satisfies the stability standards for EFSA antibiotics. Since it was reported that Bifidobacteria have resistance to aminoglycosides such as kanamycin due to the absence of a cytochrome-mediated drug transport system, EFSA does not require the MIC value of the drug for Bifidobacteria.

2) Test for Intestinal Colonization The measurement of intestinal colonization of *Bifidobacterium breve* CBT BR3 was performed in the HT-29 cell line derived from human colon epithelial cells while *Bifidobacterium breve*$^T$ (ATCC 15700) was used as a control. The HT-29 cell line was treated with each of the strains for 1 hour, and gram staining and viable cell counting were performed to compare the intestinal colonization ability between the strains. The results of the measurement are shown in Table 5 below:

TABLE 5

| | *Bifidobacterium breve* CBT BR3 | *Bifidobacterium breve*$^T$ |
|---|---|---|
| Intestinal colonization rate (%) | 91.25 | 77.24 |

The results of measurement of the intestinal colonization indicated that the *Bifidobacterium breve* CBT BR3 strain showed excellent intestinal colonization ability compared to the *Bifidobacterium breve$^T$* (ATCC 15700) strain. These results suggest that the strain of the present invention can adhere to intestinal epithelial cells to improve the intestinal environment.

3) Hemolysis Test

Figure 4:
FIG. 4 shows the results of analyzing the hemolytic activity of the *Bifidobacterium breve* CBT BR3 strain (KCTC 12201BP) according to the present invention.
Figure 5:
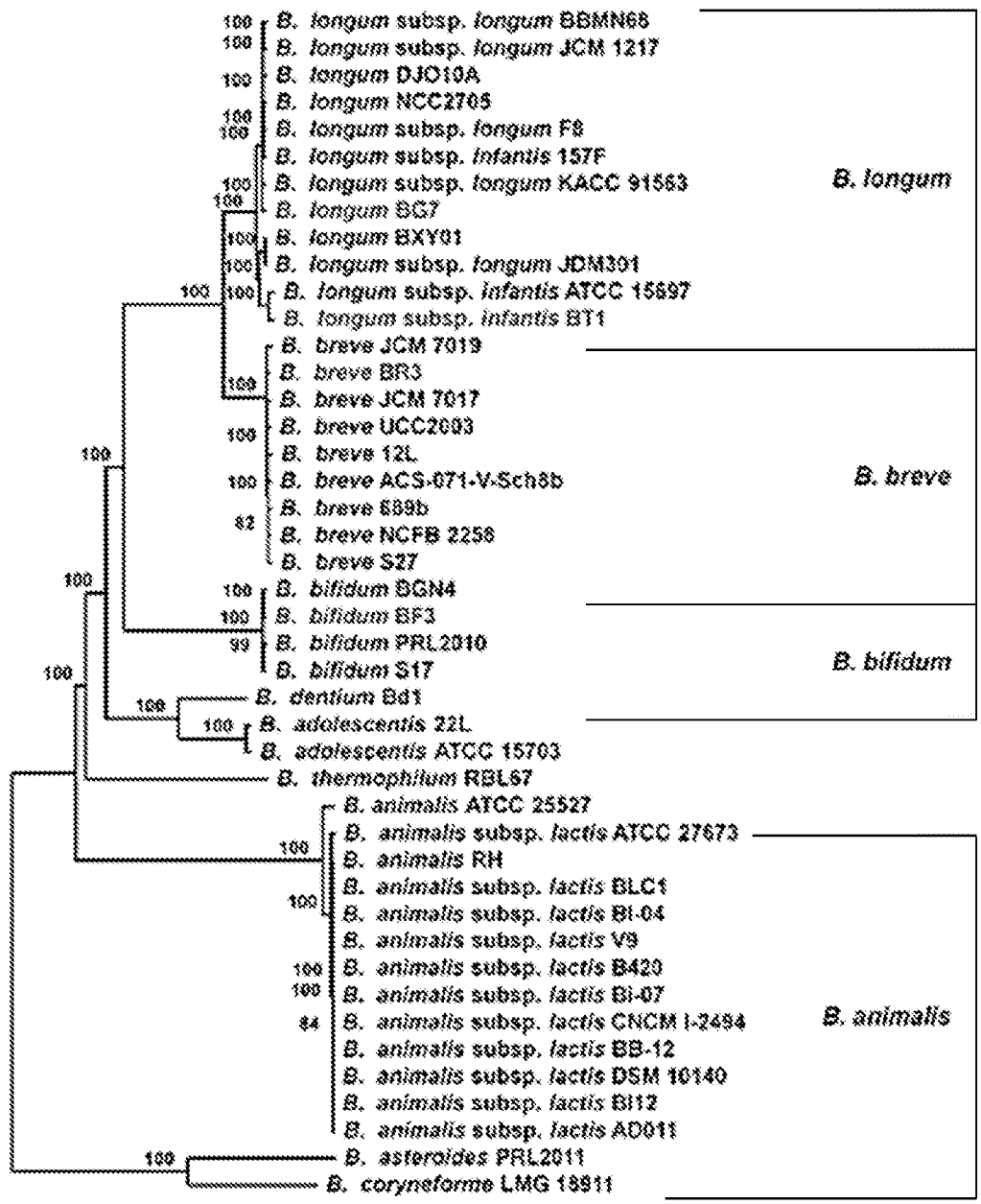
FIG. 5 shows a phylogenetic tree of the *Bifidobacterium breve* CBT BR3 strain of the present invention and related *Bifidobacterium* species.
Figure 6:
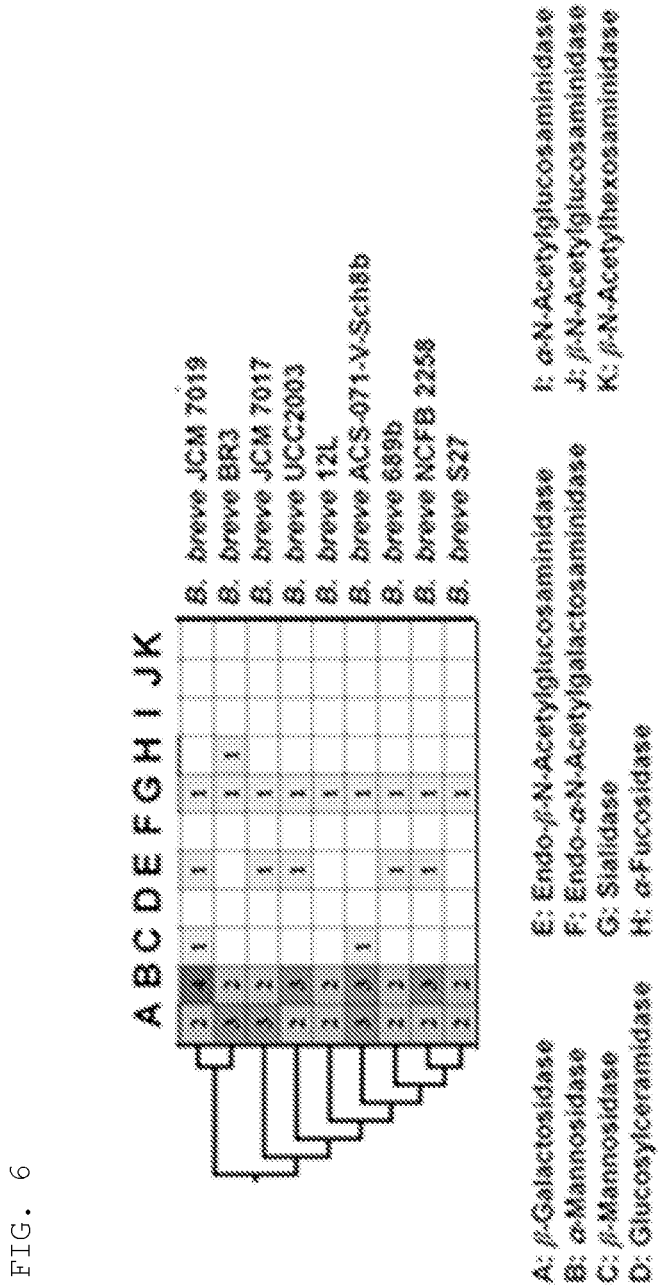
FIG. 6 shows the number of human milk oligosaccharide metabolism-related genes of the *Bifidobacterium breve* CBT BR3 strain according to the present invention.

A hemolysis test was performed in order to confirm that Bifidobacteria had no hemolytic toxicity in the human body, and in the present invention, whether erythrocytes would be destroyed or degraded (hemolysis) was examined. According to the method of Baumgartner et al., the test strain was grown in 5% horse blood-supplemented MRS medium and incubated under anaerobic conditions at 37° C. for 48 hours. Whether the strain was hemolytic was determined based on whether a transparent ring was produced around the cells. FIG. 4 shows the results of examining whether the strain of the present invention is hemolytic. As can be seen in FIG. 4, the *Bifidobacterium breve* CBT BR3 strain was not hemolytic for horse blood, indicating that the strain was harmless to the human body.

4) Acute Toxicity Test

In order to verify the safety of the *Bifidobacterium breve* CBT BR3 strain of the present invention, an acute toxicity test was performed on test animals. The lyophilized strain of the present invention was administered orally to 6-week-old male and female Sprague-Dawley (SD) rats in an amount of $1.0 \times 10^{11}$ cfu/kg. For a control group, 0.85% saline was administered intragastrically. Clinical symptoms in all the test animals were observed once a day for 14 days (a period ranging from 1 day after sample administration to the day of autopsy). The results of the observations are shown in Table 5 below.

After administration of the *Bifidobacterium breve* CBT BR3 strain, no death could be observed in all the control group and the administered group, and an animal showing specific clinical symptoms could not be found. In addition, the intake of feed and water and the body temperature were observed for 14 days after administration, and, as a result, a statistically significant difference between the administered group and the control group could not be found.

NR databases. Transfer RNA and ribosomal RNA were performed using tRNAscan-SE (Lowe and Eddy 1997) and RNAmmer (Lagesen et al. 2007), respectively. The functional classification of genes by Clusters of Orthologous Groups (COGs) category was performed using RPS-BLAST at an e-value cutoff of less than 1e-2 (Mavromatis et al. 2009).

The presence of specific genes on the genome was determined using BLASTP with a parameter of sequence homology ≥50% for a collected data set. Metabolic pathway analysis of the genome was performed using a KEGG automatic annotation server (Moriya et al. 2007). Analysis of secondary metabolite biosynthetic genes was performed using antiSMASH version 3.0.0 (Blin et al. 2013; Blin et al. 2014) (http://antismash.secondarymetabolites.org/).

2-1: HMO (Human Milk Oligosaccharide) Metabolism-Related Genes

The gene contents of the genome of the *Bifidobacterium breve* CBT BR3 strain according to the present invention were analyzed. As a result, it was found that the genome of the strain contains genes that encoded α-mannosidase, β-mannosidase, endo-β-N-acetylglucosaminidase, sialidase, and α-fucosidase, among human milk oligosaccharide metabolism-related genes. This suggests that the strain of the present invention can digest and supply human milk oligosaccharides that are not digested by human enzymes.

TABLE 7

| Strain | Enzyme | Accession number |
|---|---|---|
| B. breve CBT BR3 | Beta-galactosidase | RY69_1497 |
| B. breve CBT BR3 | Beta-galactosidase | RY69_1608 |
| B. breve CBT BR3 | Beta-galactosidase | RY69_2157 |
| B. breve CBT BR3 | Alpha-mannosidase | RY69_689 |
| B. breve CBT BR3 | Alpha-mannosidase | RY69_690 |
| B. breve CBT BR3 | Sialidase | RY69_1874 |
| B. breve CBT BR3 | Alpha-fucosidase | RY69_518 |

TABLE 6

| Sex | Strain | \multicolumn{14}{c}{Days after administration} | Death rate (%) | $LD_{50}$ |
|---|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | | |
| Male | CBT BR3 | 0 | 0 | 0 | 0 | 0 | 0 | 0 | 0 | 0 | 0 | 0 | 0 | 0 | 0 | 0 | >10$^{11}$ cfu/kg |
| | Control | 0 | 0 | 0 | 0 | 0 | 0 | 0 | 0 | 0 | 0 | 0 | 0 | 0 | 0 | 0 | |
| Female | CBT BR3 | 0 | 0 | 0 | 0 | 0 | 0 | 0 | 0 | 0 | 0 | 0 | 0 | 0 | 0 | 0 | >10$^{11}$ cfu/kg |
| | Control | 0 | 0 | 0 | 0 | 0 | 0 | 0 | 0 | 0 | 0 | 0 | 0 | 0 | 0 | 0 | |

* The numeral in Table 6 indicates the number of dead animals.

Example 2

Analysis of Genes of *Bifidobacterium breve* CBT BR3 Strain

Genome sequencing of the *Bifidobacterium breve* CBT BR3 strain (KCTC 12201BP) was performed using a PacBio RS II System (DNA Link, Republic of Korea). For the genome of the strain, a 10-kb library was constructed, and genome sequencing was performed using one of SMRT cells with C2-P4 chemistry. By the genome sequencing, a sequence having a length of 337,655,282 bp was obtained. De novo assembly was performed using SMRTpipe HGAP, and scaffolding and gap filling were performed using SMRTpipe AHA. Prediction of structural genes was performed using Glimmer3, and gene annotation was performed by AutoFACT (Koski et al. 2005) using the results obtained by BLASTP for Pfam, Uniref100, KEGG, COG and GenBank 2-2: Vitamin Biosynthetic Genes The results of the gene analysis indicated that the *Bifidobacterium breve* CBT BR3 strain of the present invention had all genes for biosynthesis of vitamins, particularly vitamins of group B. In the genome of the *Bifidobacterium breve* CBT BR3 strain of the present invention, genes capable of synthesizing two kinds of vitamins existed. It was found that the genome of the strain had genes that synthesized folate (B9) from chorismate and synthesized nicotinate (B3) from L-aspartate.

TABLE 8

A. Folate biosynthetic genes from Chorismate

| KO number | K01664 | K02619 | K13940 | K11754 |
|---|---|---|---|---|
| EC number | 2.6.1.85 | 4.1.3.38 | 2.5.1.15 | 6.3.2.12 |
| B. breve CBT BR3 | RY69_1981 | RY69_1784 | RY69_320 | RY69_563 |

TABLE 8-continued

B. Nicotinate biosynthetic genes from L-aspartate

| KO number | K00278 | K03517 | K00767 | K00763 |
|---|---|---|---|---|
| EC number | 1.4.3.16 | 2.5.1.72 | 2.4.2.19 | 6.3.4.21 |
| B. breve CBT BR3 | RY69_588 | RY69_587 | RY69_589 | RY69_1630 |

Table 9 below compares the vitamin biosynthetic genes of strains related to the present invention.

TABLE 9

| | Folate (B9)a | Folate (B9)b | Nicotinate (B3) | Riboflavin (B2) |
|---|---|---|---|---|
| B. breve JCM 7019 | — | ○ | ○ | — |
| B. breve CBT BR3 | — | ○ | ○ | — |
| B. breve JCM 7017 | — | — | ○ | — |
| B. breve UCC2003 | — | — | ○ | — |
| B. breve 12L | — | — | ○ | — |
| B. breve ACS-071-V-Sch8b | — | ○ | ○ | — |
| B. breve 689b | — | — | ○ | — |
| B. breve NCFB 2258 | — | ○ | ○ | — |
| B. breve S27 | — | — | ○ | — |

2-3: Absence of Pathogenic Gene

Analysis of PAIS (pathogenicity islands) and REIs (antimicrobial resistance islands) was performed using the PAI finder of the PAI database (Yoon et al. 2007; Yoon et al. 2015). The results of the analysis indicated that PAI (pathogenicity islands) and a PAI-like region were not present in the genome of the *Bifidobacterium breve* CBT BR3 strain of the present invention.

Example 3

Growth Promoting Effect of *Bifidobacterium breve* CBT BR3 Strain

The following example demonstrates the characteristics and growth promoting effect of the strain of the present invention. All the experimental results obtained in the Example were expressed as mean±SD, and statistical processing of the experimental results was performed using GraphPad Prism™ 6.0. In addition, the significance of difference in means between the test groups was determined by one-way ANOVA, and then the Post Hoc test was performed using Tukey's multiple range test.

3-1: Preparation of Culture of Strain of the Present Invention and Composition Containing the Same The *Bifidobacterium breve* CBT BR3 strain (KCTC 12201BP) was cultured in BL broth (BD Diagnostics, Sparks, Md.) at 37° C. for 24 hours, and diluted to $10^{11}$ CFU/ml in phosphate buffered saline (PBS, 10 mM sodium phosphate, 130 mM sodium chloride, pH 7.4). The dilution was sonicated and centrifuged to separate the supernatant, followed by filtration through a filter having a pore size of 0.45 The filtrate was freeze-dried, and then stored at −20° C. until use in vivo experiments.

3-2: Obesity Animal Model and Sampling

Animal tests were carried out in accordance with the Animal use and Care Protocol of the Institutional Animal Care and Use Committee (IACUC). As test animals, 6-week-old SD rats (10 rats per group, consisting of five male rats and five female rats) were purchased from Saeron Bio Inc. (Uiwang, Korea) and acclimated for 24 hours. Then, the rats were raised for 17 days at a temperature of 24±2° C. and a humidity of 55±15% with a 12-hr light/12-hr dark cycle. For elemental diets, the rats were allowed to take barley feed (A04, UAR, Vilemoisson-sur-Orge, France) for 17 days, and were also allowed to take drinking water alone or drinking water containing *Bifidobacterium breve* CBT BR3 ($10^7$ CFU/head/day) freely.

3-3: Growth Promoting Effect of Strain of the Present Invention

In order to observe the growth promoting effect of the *Bifidobacterium breve* CBT BR3 strain of the present invention, the rats were fed with barley feed for 17 days to induce elemental diets, and the body weight and the intake of drinking water and feed were measured each day until day 17 after the start of the experiment. The gain in the body weight was calculated by subtracting the body weight on the day of start of the experiment from the body weight on the day of measurement. The intake of each of drinking water and feed was calculated as the total intake until day 17 by measuring the intake for each cage and then calculating the intake for each rat. The efficiency of the gain in the body weight was calculated by dividing the gain in the body weight by the total intake of feed.

It was observed that, in the case of the group (CBT BR3) fed with drinking water containing *Bifidobacterium breve* CBT BR3, the body weight significantly increased from day 12 compared to that of the group (NC) normally fed with general drinking water (12 days; p<0.05, 13 to 17 days; p<0.01) (FIG. 7(A)). However, the total intake of feed (FI) for 17 days and the total intake of drinking water (WI) for 17 days showed no significant difference between the two groups (FIG. 7(B)). It can be seen that administration of the strain of the present invention did not influence the feed intake and that the weight gain (WG) was not attributable to the difference in the feed intake (FI). The ratio of weight gain to intake of feed (WG/FI) was more significant in the *Bifidobacterium breve* CBT BR3-fed group than in the normal group, indicating that the growth of the rats was promoted by administration of the *Bifidobacterium breve* CBT BR3 strain of the present invention.

The present invention has been described with a focus on the preferred embodiments thereof. Those having ordinary knowledge in the art to which the present invention pertains will appreciate that the present invention may be embodied in various modified or changed forms without departing from the essential features of the present invention. Therefore, the true range of protection of the present invention should be defined by the attached claims and equivalents thereto rather than by the above-described embodiments.

The invention claimed is:

1. A method for alleviating one or more conditions selected from the group consisting of growth retardation, development retardation, and low body weight in a subject selected from the group consisting of human neonates, infants, and growing children, comprising:
   administering to the subject a nutraceutical composition that comprises:
      an effective amount of *Bifidobacterium breve* CBT BR3 strain deposited under accession number KCTC 12201BP; and
      an excipient or a carrier,
      wherein said bacteria strain is lyophilized.

2. The method according to claim 1, further comprising orally administering a prebiotic substance.

3. The method according to claim 2, wherein said nutraceutical composition comprises the prebiotic substance.

4. The method according to claim 2, wherein said nutraceutical composition further comprises at least one additives selected from the group consisting of a binder, a disintegrant, and a lubricant.

5. The method according to claim 1,
   wherein an active ingredient in said nutraceutical composition for alleviating the one or more conditions consists of:
   *Bifidobacterium breve* CBT BR3 strain deposited under accession number KCTC 12201BP and
   at least one selected from the group consisting of *Bifidobacterium longum* subsp. *infantis* CBT BT1 (KCTC 11859BP) and/or and *Bifidobacterium bifidum* CBT BF3 (KCTC 12199BP).

* * * * *

SEQUENCE LISTING

<160> NUMBER OF SEQ ID NOS: 1

<210> SEQ ID NO 1
<211> LENGTH: 1524
<212> TYPE: DNA
<213> ORGANISM: Bifidobacterium breve -continued

```
<400> SEQUENCE: 1
agagtttgat cctggctcag gatgaacgca ggcggcgtgc ttaacacatg caagtcgaac      60
gggatccatc gggctttgct tggtggtgag agtggcgaac gggtgagtaa tgcgtgaccg     120
acctgcccca tgcaccggaa tagctcctgg aaacgggtgg taatgccgga tgctccatca     180
caccgcatgg tgtgttggga aagcctttgc ggcatgggat ggggtcgcgt cctatcagct     240
tgatggcggg gtaacggccc accatggctt cgacgggtag ccggcctgag agggcgaccg     300
gccacattgg gactgagata cggcccagac tcctacggga ggcagcagtg gggaatattg     360
cacaatgggc gcaagcctga tgcagcgacg ccgcgtgagg gatggaggcc ttcgggttgt     420
aaacctcttt tgttagggag caaggcactt tgtgttgagt gtacctttcg aataagcacc     480
ggctaactac gtgccagcag ccgcggtaat acgtagggtg caagcgttat ccggaattat     540
tgggcgtaaa gggctcgtag gcggttcgtc gcgtccggtg tgaaagtcca tcgcttaacg     600
gtggatccgc gccgggtacg ggcgggcttg agtgcggtag gggagactgg aattcccggt     660
gtaacggtgg aatgtgtaga tatcgggaag aacaccaatg gcgaaaggca ggtctctggg     720
ccgttactga cgctgaggag cgaaagcgtg gggagcgaac aggattagat accctggtag     780
tccacgccgt aaacggtgga tgctggatgt ggggcccgtt ccacgggttc cgtgtcggag     840
ctaacgcgtt aagcatcccg cctggggagt acggccgcaa ggctaaaact caaagaaatt     900 gacggggggcc cgcacaagcg gcggagcatg cggattaatt cgatgcaacg cgaagaacct     960
tacctggcct tgacatgttc ccgacgaccc cagagatggg gtttccttc ggggcgggtt    1020 cacaggtggt gcatggtcgt cgtcagctcg tgtcgtgaga tgttgggtta agtcccgcaa    1080
cgagcgcaac cctcgccccg tgttgccagc ggattatgcc gggaactcac ggggaccgc    1140 cggggttaac tcggaggaag gtggggatga cgtcagatca tcatgcccct tacgtccagg    1200
gcttcacgca tgctacaatg gccggtacaa cgggatgcga cagtgcgagc tggagcggat    1260
ccctgaaaac cggtctcagt tcggatcgca gtctgcaact cgactgcgtg aaggcggagt    1320
cgctagtaat cgcgaatcag caacgtcgcg gtgaatgcgt tcccgggcct tgtacacacc    1380
gcccgtcaag tcatgaaagt gggcagcacc cgaagccggt ggcctaaccc cttgcgggag    1440
ggagccgtct aaggtgaggc tcgtgattgg gactaagtcg taacaaggta gccgtaccgg    1500
aaggtgcggc tggatcacct cctt                                           1524
```